United States Patent [19]

Ribi

[11] Patent Number: 4,629,722
[45] Date of Patent: Dec. 16, 1986

[54] METHOD OF INHIBITING THE ONSET OF ACUTE RADIATION SYNDROME

[75] Inventor: Edgar E. Ribi, Hamilton, Mont.

[73] Assignee: Ribi ImmunoChem Research, Inc., Hamilton, Mont.

[21] Appl. No.: 630,013

[22] Filed: Jul. 12, 1984

[51] Int. Cl.$^4$ .............................................. A61K 37/02
[52] U.S. Cl. .......................................... 514/2; 514/7; 514/917; 514/921; 424/88; 424/92
[58] Field of Search ..................... 424/88, 92; 514/917, 514/2, 921, 7; 260/112 R

[56] References Cited

U.S. PATENT DOCUMENTS 4,436,728  3/1984  Rabi et al. ........................ 260/112 R

OTHER PUBLICATIONS

CA. No. 185374h, vol. 88, 1978, Relation between Four Types of Radiation Damage and Induced Repair, Radar.
Ziegler et al., Treatment of Gram-Negative Bacteremia and Shock . . . E. coli, Zama, vol. 307(20) 1982, p. 1225.
CA. No. 956n, vol. 87, 1977, Experimental Septic Shock, Hinshaw et al.
CA. No. 86685(q), vol. 97, 1982, Effect of Pretreatment . . . Dogs, Balogh et al.
CA. No. 103796x, vol. 101, Prevention of . . . Shock . . . Endotoxin Pretreatment, Balogh.
CA. No. 204517s, vol. 100, Bacterial Endotoxins . . . Resistance, Larand.

*Primary Examiner*—John Kight
*Assistant Examiner*—Garnette D. Draper
*Attorney, Agent, or Firm*—Burgess, Ryan & Wayne

[57] ABSTRACT

The present invention is directed to a method of inhibiting the onset of acute radiation syndrome caused by the exposure of warm-blooded animals to a whole body dose of at least about 100 rads of x-radiation. The invention is also directed to a method of inhibiting the onset of septicemia. The methods comprise administering to a warm-blooded animal an effective amount of a pharmaceutical composition comprising refined detoxified endotoxin in combination with a pharmaceutically acceptable carrier.

5 Claims, No Drawings

METHOD OF INHIBITING THE ONSET OF ACUTE RADIATION SYNDROME

BACKGROUND OF THE INVENTION

The present invention is directed to a method of inhibiting the onset of acute radiation syndrome caused by the exposure of warm-blooded animals to a whole body dose of at least about 100 rads of X-radiation. The present invention is also directed to a method of inhibiting the onset of septicemia. Each of said methods comprising administering to a warm-blooded animal an effective amount of a pharmaceutical composition comprising refined detoxified endotoxin (RDE) in combination with a pharmaceutically acceptable carrier.

The exposure of a warm-blooded animal to a whole body dose of at least about 100 rads of X-radiation results in the onset of a complex set of symptoms termed acute radiation syndrome. The nature and severity of acute radiation syndrome is directly related to the dose of X-radiation to which the warm-blooded animal is exposed. However, it is generally recognized that the haemopoetic system, which is responsible for blood cell production, is the most severely damaged.

The single most important consequence of haemopoetic destruction following high level radiation exposure is that antimicrobial immunity is severely compromised with respect to both exogenous and endogenous microorganisms. Following irradiation with high levels of X-radiation, all warm-blooded animals, including man, are more susceptible to a broad spectrum of bacteria, viruses, protozoans, etc., as discussed in "Beneficial Effects of Endotoxins", edited by Alois Nowatny, pg. 127–148, Plenum Press, 1983.

In order to combat the toxic effect of X-radiation, it is necessary to stimulate the production and differentiation of granulocytes (granulopoiesis). Granulocytes are white blood cells such as macrophages, monocytes, eosinophils and basophils. It is known that the blood contains a factor, known as colony stimulating factor (CSF) which is necessary for granulopoiesis. Colony stimulating factor is described in Chervenick, P. A. et al., Science 118 164, 1972; and Golde, D. W. et al., Lancet 2, 1397, 1972, incorporated herein by reference. Therefore, the degree to which the blood exhibits colony stimulating factor is directly correlated to the ability of the body to withstand high doses of radiation.

Septicemia is a clinical syndrome in which infection is disseminated through the body by the blood stream. It is a potentially disastrous blood infection that can be caused by a variety of bacteria. It is a pathological state which results from the presence of microorganisms and/or their poisonous by-products in the blood stream.

A survey in 1974 reported that septicemia strikes 71,000 people in the United States annually resulting in death in approximately 25% of the cases. One of the major causes of septicemia is the result of post-operative infection resulting from endogenous bacteria from the respiratory or gastrointestinal tract (See Cruse, P. J. E., et al. Arch., Surg. 107, 106–210, 1973), incorporated herein by reference.

Refined detoxified endotoxin (RDE) is characterized as having no detectable 2-keto-3-deoxyoctanoate, between about 350 and 475 nmoles/mg of phosphorus and between about 1700 and 2000 nmoles/mg of fatty acids. RDE is a significant improvement over endotoxic extracts obtained from Enterobacteriaciae because RDE is detoxified and therefore does not contain the highly toxic components which have rendered endotoxic extracts unsuitable for therapeutic use (See *Peptides as Requirements for Immunotherapy of the Guinea-Pig Line-10 Tumor with Endotoxins;* Ribi, et al. Cancer Immunol. Immunother. Vol. 7, pgs 43–58 (1979)) incorporated herein by reference. The beneficial effects of RDE over other endotoxic extracts is described for example in U.S. Pat. Nos. 4,436,727 and 4,436,728; and Ribi, E. Journal of Biological Response Modifiers 3:1–9, Raven Press, (1984), incorporated herein by reference.

It is therefore an object of the invention to provide a method of inhibiting the onset of acute radiation syndrome in warm-blooded animals which are exposed to a whole body dose of at least about 100 rads of X-radiation using a therapeutic composition containing refined detoxified endotoxin.

It is another object of the invention to provide a method of inhibiting the onset of septicemia in warm-blooded animals using a therapeutic composition containing refined detoxified endotoxin.

SUMMARY OF THE INVENTION

The present invention is directed to a method of inhibiting the onset of acute radiation syndrome in a warm-blooded animal which arises from exposure of the warm-blooded animal to a whole body dose of at least about 100 rads of X-radiation, which comprises administering to the warm-blooded animal, prior to exposure to said dose of X-radiation, an effective amount of a composition comprising refined detoxified endotoxin and a pharmaceutically acceptable carrier. The present invention is also directed to a method of inhibiting the onset of septicemia in warm-blooded animals comprising administering to said warm-blooded animals, an effective amount of a composition comprising refined detoxified endotoxin and a pharmaceutically acceptable carrier.

DETAILED DESCRIPTION OF THE INVENTION

Refined detoxified endotoxin as employed in the present invention can be prepared in the manner set forth in U.S. Pat. Nos. 4,436,727 and 4,436,728 incorporated herein by reference. More specifically, endotoxin extracts of the type used as the starting material to produce RDE may be obtained from any Enterobacteriaciae including parent organisms and mutants. The aforesaid patents describes the type of microorganisms that may be used to obtain the starting material and several methods for preparing the starting material. The preferred method of obtaining the endotoxic extract is that disclosed by Chen et al., J. Infect. Dis 128 543 (1973).

RDE as prepared above is combined with a pharmaceutically acceptable carrier such as, for example, a phosphate buffer saline solution, which can be injected parenterally (e.g. intravenously, intraperitoneally, or intramuscularly). The instant composition contains from about 1 to 1000 micrograms of RDE, preferably about 25 to 200 micrograms, based on administration to a typical 70 kg adult patient. The composition can be administered to patients once, twice or three times a week and the number of administrations is usually about twice or three times.

The RDE containing composition when used to inhibit the onset of acute radiation syndrome should be administered at least about 24 hours before the warm-blooded animal is exposed to the high dose of radiation of at least about 100 rads, preferably between about 24 and 48 hours.

EXAMPLE 1

Assay for induction of Colony Stimulating Factor (CSF) in Vivo

Three groups of NMRI mice (each group containing five mice) were each injected intravenously with five micrograms of the test substance identified in Table 1.

TABLE 1

| Substance | Colonies (X + standard deviation)* |
|---|---|
| Refined Detoxified Endotoxin from S. minnesota R595 | 80 ± 3.6 |
| Refined Detoxified Endotoxin S. typhimurium G30/C21 | 72 ± 9.3 |
| Saline Control | 0 |

*arithmetic mean of X number of colonies + on - standard deviation

Blood was obtained from the plexus orbitalis two hours after injection and subsequently assayed in triplicate to determine the CSF content. The assay method is described in Metcalf, D. and Moore, M. A., in *Haemopoetic Cells*, North Holland Publishing Company, Amsterdam, Holland, 1971. The CSF content was expressed as the number of colonies in $10^5$ nucleated bone marrow cells/ml. As shown in Table 1, the two groups of mice injected with RDE showed significant CSF activity while the control group, injected only with a saline solution, showed no CSF activity. The foregoing test establishes that RDE stimulates the production of CSF which is necessary for the production and differentiation of granulocytes (granulopoiesis).

EXAMPLE 2

Protection Against X-Radiation

Two groups of C3HeB/FeJ mice (each group being composed of 20 mice) were each injected intravenously with the test substance shown in Table 2. The mice were injected 24 hours before irradiation with 600 rads of X-radiation at the rate of 70 rads per minute. A third group of 20 mice (control) were not injected with a test substance and were exposed to irradiation in the same manner as the above-mentioned two groups of mice.

As noted in Nowatny, A. page 127, the peak incidence of mortality for a mid-lethal dose of X-radiation occurs between 10 and 14 days following irradiation. Accordingly, it was expected that both the control animals and those treated with RDE prior to exposure, would survive the first 10 days after exposure to the high level of radiation described above. After 15 days, 85% of those treated with RDE survived exposure while only 55% of the control animals survived. 20 days subsequent to exposure, 70–75% of the RDE treated mice remained alive while only 25% of the control animals survived. Accordingly, RDE is a significant factor in reducing the risk of death after exposure to high levels of radiation.

TABLE 2

| Preparation | Dose (μg) | Number of animals | Percent survivors on day 10 | 15 | 20 | 30 |
|---|---|---|---|---|---|---|
| Control | — | 20 | 100 | 55 | 25 | 20 |
| RDE-S. minnesota | 100 | 20 | 100 | 85 | 75 | 75 |
| RDE-S. typhimurium | 100 | 20 | 100 | 85 | 70 | 65 |

EXAMPLE 3

Protection Against the Onset of Septicemia

14 NMRI mice were pretreated with one microgram of RDE administered by intraperitoneal injection. 24 hours later each of the mice underwent surgery wherein the cecum of each mouse was ligated and punctured to internally expose the mice to microorganisms capable of instigating the onset of septicemia. Upon completion of surgery, the animals were observed for 120 hours. A second group of mice were subjected to surgery in precisely the same way without pretreatment with RDE. The results are shown in Table 3. 71% of the RDE treated mice survived 120 hours after induction of septicemia. Those mice which did not receive pretreatment with RDE exhibited only a 21% survival rate.

The foregoing results show that RDE inhibits the onset of septicemia.

NONSPECIFIC RESISTANCE TO SEPTICEMIA INDUCED IN MICE BY CECAL LIGATION AND PUNCTURE

| Pretreatment 1 μg, ip, 24 hr prior surgery | 120 hrs after induction of septicemia Dead/Total | % Survival |
|---|---|---|
| None | 11/14 | 21 |
| RDE(S. typhimurium) | 4/14 | 71 |

What is claimed is:

1. A method of inhibiting the onset of acute radiation syndrome in a warm-blooded animal which arises from exposure of said warm-blooded animal to a whole body dose of at least 100 rads of x-radiation comprising administering to said warm-blooded animal prior to exposure to said X-radiation an effective amount of a composition consisting of:
   (a) refined detoxified endotoxin containing no detectable 2-keto-3-deoxyoctanoate and having between about 350 and 475 nmoles/mg of phosphorus and between about 1700 and 2000 nmoles/mg of fatty acids; and
   (b) a pharmaceutically acceptable carrier.
2. The method of claim 1, wherein the composition is in the form of a phosphate buffer saline solution.
3. The method of claim 1, wherein the composition is administered parenterally.
4. The method of claim 1, wherein said effective amount of the composition is between about 1 and 1000 mcg.
5. The method of claim 4, wherein said effective amount of the composition is between about 25 and 200 mcg.

* * * * *